United States Patent
Gallo, Sr. et al.

(10) Patent No.: US 8,425,506 B2
(45) Date of Patent: Apr. 23, 2013

(54) ASPIRATING ELECTROSURGICAL PROBE WITH ASPIRATION THROUGH ELECTRODE FACE

(75) Inventors: David P. Gallo, Sr., Naples, FL (US); Philip S. O'Quinn, Naples, FL (US)

(73) Assignee: Arthrex, Inc., Naples, FL (US)

(*) Notice: Subject to any disclaimer, the term of this patent is extended or adjusted under 35 U.S.C. 154(b) by 1058 days.

(21) Appl. No.: 11/636,548

(22) Filed: Dec. 11, 2006

(65) Prior Publication Data

US 2007/0149965 A1   Jun. 28, 2007

Related U.S. Application Data

(60) Provisional application No. 60/749,600, filed on Dec. 13, 2005.

(51) Int. Cl.
*A61B 18/18* (2006.01)
(52) U.S. Cl.
USPC .................................. 606/41; 606/45; 606/49
(58) Field of Classification Search ............ 606/45, 606/48, 49–50
See application file for complete search history.

(56) References Cited

U.S. PATENT DOCUMENTS

| | | | | |
|---|---|---|---|---|
| 6,379,350 | B1 * | 4/2002 | Sharkey et al. | 606/41 |
| 6,575,968 | B1 | 6/2003 | Eggers et al. | |
| 6,837,884 | B2 | 1/2005 | Woloszko | |
| 7,276,063 | B2 * | 10/2007 | Davison et al. | 606/41 |
| 7,837,683 | B2 * | 11/2010 | Carmel et al. | 606/41 |
| 2001/0031963 | A1 | 10/2001 | Sharkey et al. | |
| 2002/0049438 | A1 | 4/2002 | Sharkey et al. | |
| 2004/0030330 | A1 | 2/2004 | Brassell et al. | |
| 2004/0193150 | A1 | 9/2004 | Sharkey et al. | |
| 2004/0230190 | A1 | 11/2004 | Dahla et al. | |
| 2005/0234446 | A1 | 10/2005 | Van Wyk et al. | |
| 2005/0277915 | A1 | 12/2005 | DeCesare et al. | |
| 2006/0259031 | A1 | 11/2006 | Carmel et al. | |

FOREIGN PATENT DOCUMENTS

| WO | 03/068095 | * 8/2003 |
|---|---|---|
| WO | WO 2006/124624 | 11/2006 |

OTHER PUBLICATIONS

PCT International Search Report for International application No. PCT/US06/18479 mailed Jul. 27, 2007.

* cited by examiner

*Primary Examiner* — Linda Dvorak
*Assistant Examiner* — Jaymi Della
(74) *Attorney, Agent, or Firm* — Carlson, Gaskey & Olds, P.C.

(57) ABSTRACT

A high efficiency electrosurgical electrode with an advanced electrically conductive tip and aspiration port, and a method of conducting an electrosurgical procedure with such electrode. The electrosurgical electrode comprises an electrically conductive tip with a central lumen or "chimney" surrounded by a plurality of protuberances. The central lumen or "chimney" is "self-cleaning" and/or "self-clearing" in that any tissue passing through the central lumen that might cause a clog is quickly denatured by the surrounding electrode and aspirated from the ablation site, so that the probe does not require special consideration by the user (for example, replacement due to total loss of suction). The plurality of protuberances have various forms and geometries that define a plurality of recesses and that, in one embodiment, are provided in a "star-shaped" or partial "star-shaped" pattern.

24 Claims, 9 Drawing Sheets

ASPIRATING ELECTROSURGICAL PROBE WITH ASPIRATION THROUGH ELECTRODE FACE

The present application claims the benefit of U.S. Provisional Application Ser. No. 60/749,600, filed on Dec. 13, 2005, the disclosure of which is incorporated by reference herein in its entirety.

FIELD OF THE INVENTION

The present invention relates to the field of electrosurgery and, in particular, to electrosurgical devices and methods which employ high frequency voltage to cut, ablate or coagulate tissue in a fluid environment.

BACKGROUND OF THE INVENTION

Radiofrequency (RF) probes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical device, both the active and the return current electrodes are exposed and are typically in close proximity. The RF current flows from the active electrode to the return electrode through the tissue. Thus, in contrast with the monopolar electrosurgical devices, the return current path for a bipolar device does not pass through the patient's body except for close proximity to the tip of the electrode.

Electrosurgery is the intentional passage of high frequency current through tissue to achieve a controlled surgical effect. This can be accomplished in an oxygen rich, an inert gas, or a conductive fluid media environment. Arthroscopic tissue ablation is performed in a conductive fluid environment, such as inside of a joint or body cavity filled with, for instance, normalized saline solution, and differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in the proximity of the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode anytime that the probe is energized. This is in contrast to conventional surgery (also called "open surgery") in which current flows only through electrode surfaces in contact with the patient's tissue.

During the past several years, specialized arthroscopic electrosurgical probes also called ablators have been developed for arthroscopic surgery. Ablators differ from the conventional arthroscopic electrosurgical probes in that they are designed for the bulk removal of tissue by vaporization, rather than by cutting the tissue or coagulating the bleeding vessels. This way, during ablation, volumes of tissue are vaporized rather then discretely cut out and removed from the surgical site. Aspiration ports in the ablator are often provided to remove ablated tissue and debris.

The power requirements of ablators are generally higher than those of other arthroscopic probes. The efficiency of the probe design and the characteristics of the radio frequency (RF) power supplied to the probe also affect the amount of power required for ablation. For example, probes with inefficient designs and/or powered by RF energy with poorly suited characteristics will require higher powers levels than those with efficient designs and appropriate generators. Probes used in electrosurgery have relatively large area of metallic electrode, which is the active area of the probe. Large electrode area decreases the probe impedance and, therefore, increases the RF power required for proper operation. The shape of the dielectric insulator and of the probe tip can significantly affect ablation. By properly shaping the insulator and the electrode tip, the threshold power can be substantially decreased.

A recent improvement to ablation electrodes is the addition of aspiration to remove bubbles and debris from the surgical site. During electrosurgery in a conductive fluid environment, tissue is vaporized, thereby producing steam bubbles which may obscure the view of the surgeon or displace saline from the area of the intra-articular space which the surgeon wishes to affect. In the case of ablation (bulk vaporization of tissue), the number and volume of bubbles produced is even greater than when using other electrodes since fluid is continually boiling at the active electrode during use. Ideally, flow through the joint carries these bubbles away; however, in certain procedures this flow is frequently insufficient to remove all of the bubbles. Aspiration removes some bubbles as they are formed by the ablation process, and others after they have collected in pockets within the joint. The aspiration portal is connected to an external vacuum source which provides suction for bubble evacuation.

Aspirating ablators are divided into two categories according to their level of flow. High-flow ablators have an aspiration tube, the axis of which is coaxial with the axis of the ablator rod or tube, which draws in bubbles and fluid through its distal opening and/or openings cut into the tube wall near its distal tip. High-flow ablators may decrease the average joint fluid temperature by removing heated saline (waste heat since it is an undesirable biproduct of the process) from the general area in which ablation is occurring. The effectiveness of the aspiration, both for removal of bubbles and for removal of waste heat, will be affected by the distance between the opening through which aspiration is accomplished and the active electrode. The distal tip of the aspiration tube is generally several millimeters distant proximally from the active electrode so as to not to obstruct the surgeon's view of the electrode during use. Decreasing this distance is desirable since doing so will increase the effectiveness of the aspiration. However, this must be accomplished without limiting the surgeon's view or decreasing the ablator's ability to access certain structures during use.

Low-flow ablators are those which aspirate bubbles and fluid through gaps in the ablating surfaces of the active electrode and convey them from the surgical site via means in the elongated distal portion of the device. Current low-flow ablators require increased power to operate as effectively as a nonaspirating or high-flow aspirating ablators because the low-flow aspiration draws hot saline from the active site of a thermal process. In the case of low-flow ablators, the heat removed is necessary process heat rather than the waste heat removed by high-flow ablators. Because of this, aspirating ablators of the low-flow type generally require higher power levels to operate than other ablators thereby generating more waste heat and increasing undesirable heating of the fluid within the joint.

Each of these types of aspirating ablation electrodes has its drawbacks. In the case of high-flow aspirating ablators, the aspiration tube increases the diameter of the device thereby necessitating the use of larger cannulae which, in turn, results in an increase in wound size and often an increase in patient pain and recovery time. In the case of low-flow aspirating ablators, the devices decrease the efficiency of the probes since process heat is removed from a thermal process. This decreased efficiency results in decreased rates of tissue removal for a given power level. This results in increased procedure times or necessitates the use of higher power levels to achieve satisfactory tissue removal rates. High power levels are undesirable as they cause increased heating of the fluid at the site and thereby increase the likelihood of thermal injury to the patient.

Accordingly, it is desirable to provide an electrosurgical probe of high efficiency and high impedance with an improved design of the aspiration port, and which is capable of conferring high ablation rates at low RF power levels. An electrosurgical ablation electrode, which aspirates through the ablating portion of the active electrode and has increased ablation efficiency as compared to existing ablation electrodes which aspirate through the active electrode, is also desirable.

SUMMARY OF THE INVENTION

The present invention overcomes the disadvantages of the prior art by providing a high efficiency electrosurgical probe with an advanced tip and insulator design that achieves high ablation rates at low RF power levels, and consistent and aggressive suction.

The electrosurgical probe of the present invention comprises a metallic tip and a dielectric insulator adjacent the metallic tip. The metallic tip and dielectric material are designed to reduce the surface area of the electrode and to form a high current density zone at the tip of the probe to increase the efficiency of the probe. According to one embodiment, the metallic tip is provided with a central lumen or "chimney" for directing aspiration flow that allows surgical fluids and debris to be aspirated from an ablation site. The central lumen or "chimney" is "self-cleaning" and/or "self-clearing" in that any tissue passing through the central lumen that might cause a clog is quickly denatured by the surrounding electrode and aspirated from the ablation site, so that the probe does not require special consideration by the user (for example, replacement due to total loss of suction). The central lumen for directing aspiration flow is circumferentially surrounded by a plurality of protuberances having various geometries and being spaced from each other by a plurality of grooves. Preferably, the protuberances are provided in a "star-shaped" or partial "star-shaped" pattern.

In another aspect, the invention provides an apparatus for conducting electrosurgical procedures or interventions comprising at least one electrosurgical probe that includes a shaft having a proximal end and a distal end. The distal end supports at least one electrosurgical probe comprising a metallic electrode having a metallic tip. The metallic tip comprises a central lumen or "chimney" for directing aspiration flow that allows surgical fluids and debris to be aspirated from an ablation site, surrounded by a plurality of protuberances of various geometrical forms that are spaced from each other by a predetermined distance and are surrounded by air. Preferably, the protuberances are provided in a "star-shaped" or partial "star-shaped" pattern.

The invention also provides a method of employing an electrosurgical probe with decreased area of metallic electrode and increased efficiency in an electrosurgical procedure. The method comprises the steps of: (i) positioning an electrosurgical probe adjacent a target tissue, the electrosurgical probe comprising an electrode having a central lumen or "chimney" which has "self-cleaning" and/or "self-clearing" capabilities and which directs aspiration flow surrounded by a plurality of protuberances spaced apart from each other and surrounded by air, the protuberances being provided in a "star-shaped" or partial "star-shaped" pattern, and then (ii) either submerging the target tissue in an electrical conducting fluid or (iii) directing an electrically conducting fluid to the target tissue to ablate tissue in the region adjacent the electrode.

Other features and advantages of the present invention will become apparent from the following description of the invention which refers to the accompanying drawings.

DETAILED DESCRIPTION OF THE PREFERRED EMBODIMENT

The present invention provides an electrosurgical probe with an electrosurgical electrode having an advanced metallic tip design and being capable of achieving high ablation rates at low RF power supply.

The electrosurgical probe comprises a metallic tip and a dielectric insulator adjacent the metallic tip. The metallic tip and dielectric material are designed to reduce the surface area of the electrode and to form a high current density zone at the tip of the probe to increase the efficiency of the probe. According to an exemplary embodiment, the metallic tip is provided with a central lumen or "chimney" for directing aspiration flow that allows surgical fluids and debris to be aspirated from an ablation site. By positioning the suction port in the center of, and surrounded by, the active electrode, the central lumen or "chimney" becomes "self-cleaning" and/or "self-clearing" in that any tissue passing through the central lumen that might cause a clog is quickly denatured by the surrounding electrode and aspirated from the ablation site, so that the probe does not require special consideration by the user (for example, replacement due to total loss of suction). In this manner, any potential aspiration clog is cleared by a combination of the continued transference of heat created as a byproduct of the RF therapeutic effect, which causes tissue in the suction port to become denatured and then forcefully drawn through the device by the vacuum.

The central lumen for directing aspiration flow is circumferentially surrounded by a plurality of protuberances having various geometries and being preferably provided in a "star-shaped" or partial "star-shaped" pattern, the protuberances being spaced from each other by a plurality of grooves. As a result of the self-cleaning central lumen or "chimney" that directs aspiration flow and further as a result of the protuberances provided in a "star-shaped" or partial "star-shaped" pattern surrounding such self-cleaning central lumen, the electrosurgical probe of the present invention provides consistent, aggressive suction, and is able to maintain a cool environment, while also delivering a controlled therapeutic effect at low power.

Figure 22:
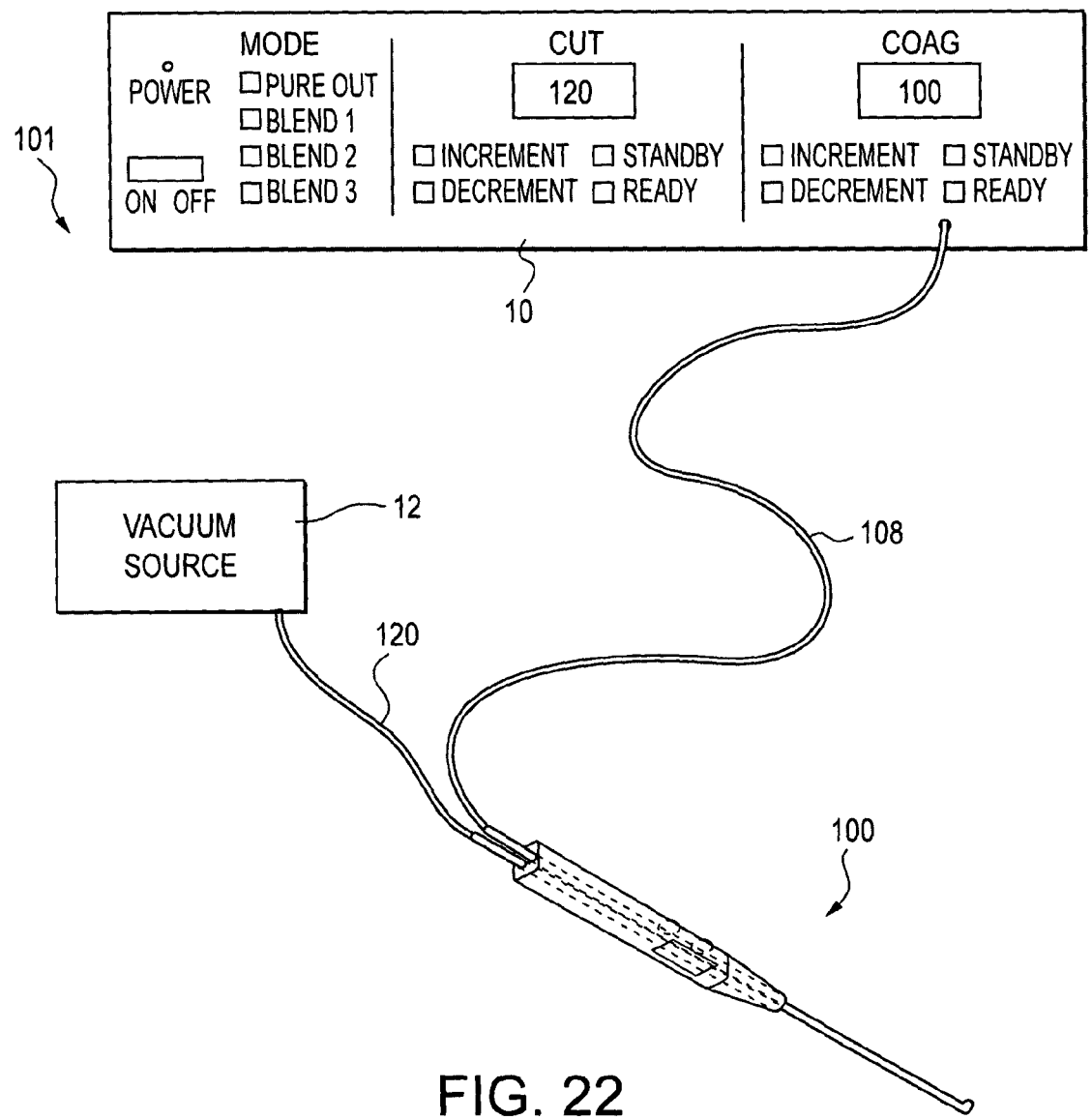
FIG. 22 is a schematic representation of the electrosurgical system according to the principles of the present invention.

Referring now to the drawings, where like elements are designated by like reference numerals, an electrosurgery system 101 constructed in accordance with the principles of this invention is depicted in FIG. 22. Electrosurgical probe 100 (also called "ablation electrode," "ablator" or "probe") is connected by electrical cable 108 to electrosurgical generator 10, and by tube 120 to an external vacuum source 12. A return electrode (not shown) is connected to the electrosurgical generator to provide a return path for the RF energy. The return electrode may be a dispersive pad attached to the patient at a site remote from the surgical site, or may be in proximity to the active electrode in contact with tissue or the conductive liquid.

Figure 1:
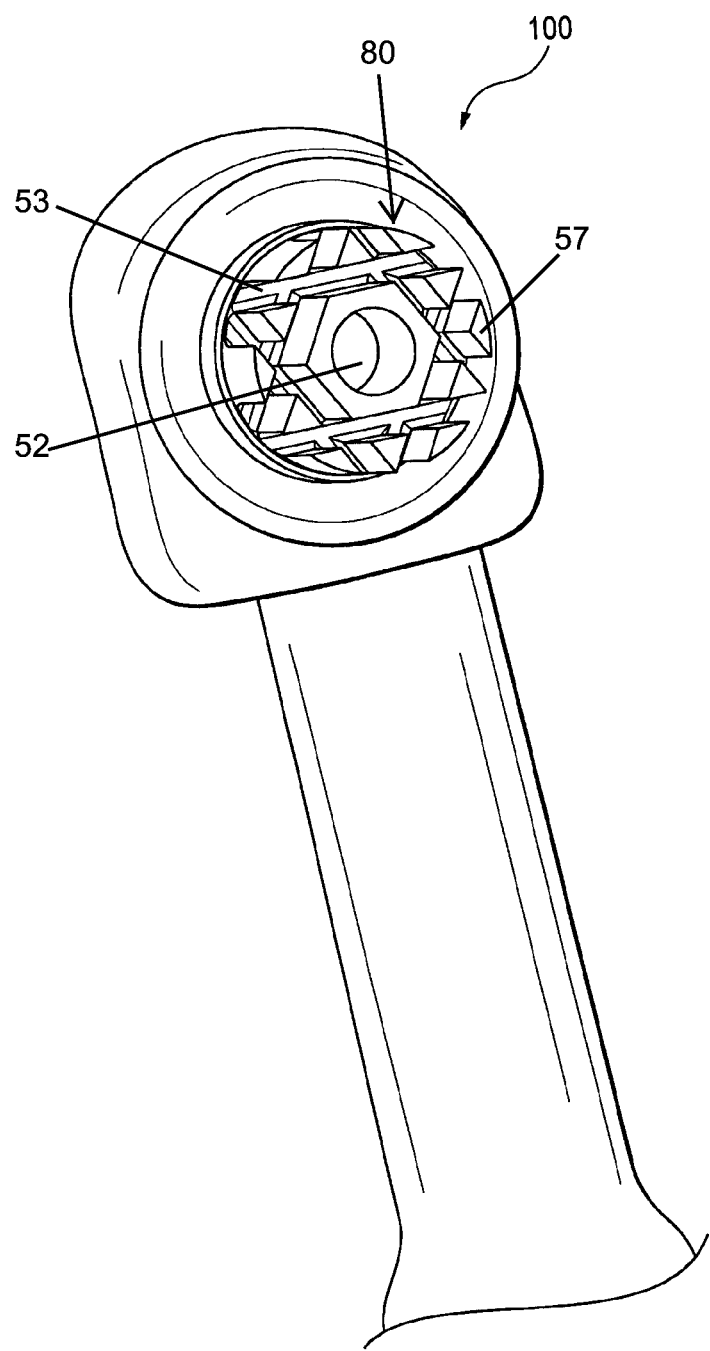
FIG. 1 illustrates a perspective view of the tip of an electrosurgical probe according to a first embodiment of the present invention.
Figure 2:
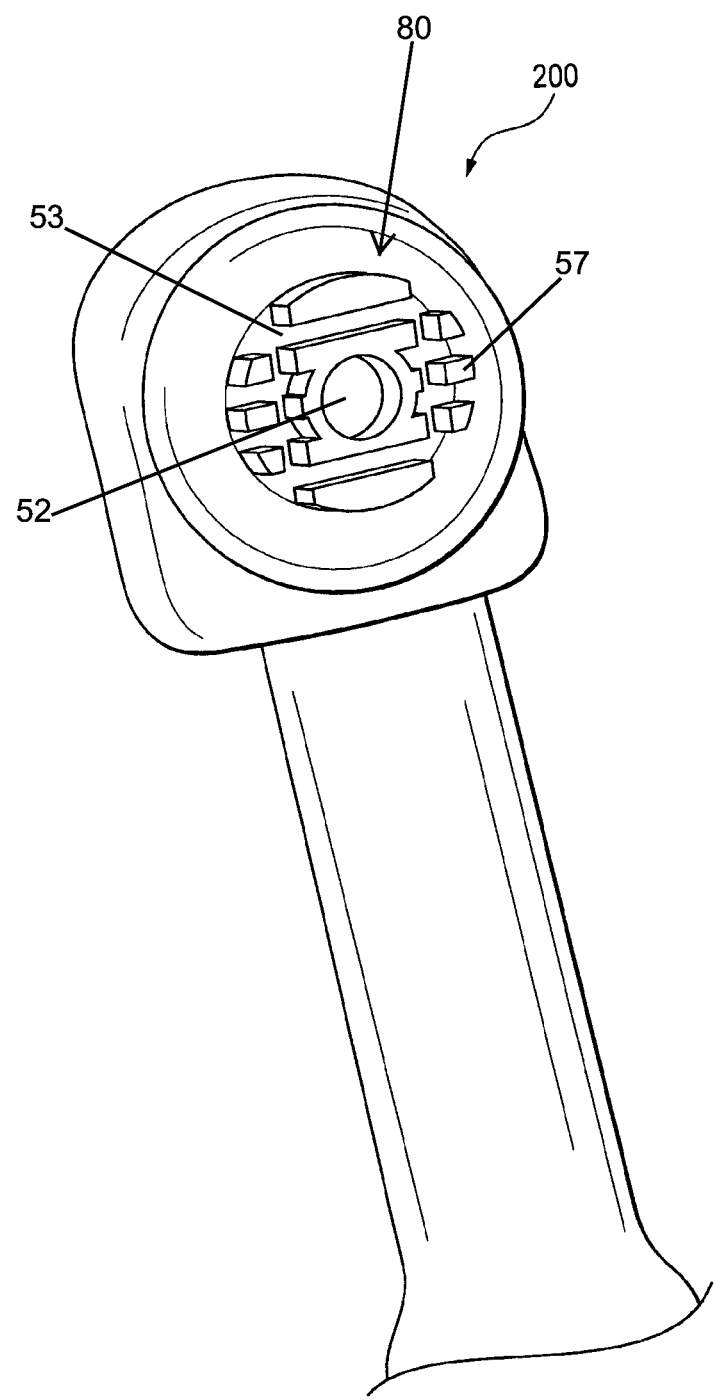
FIG. 2 illustrates a perspective view of the tip of an electrosurgical probe according to a second embodiment of the present invention.
Figure 3:
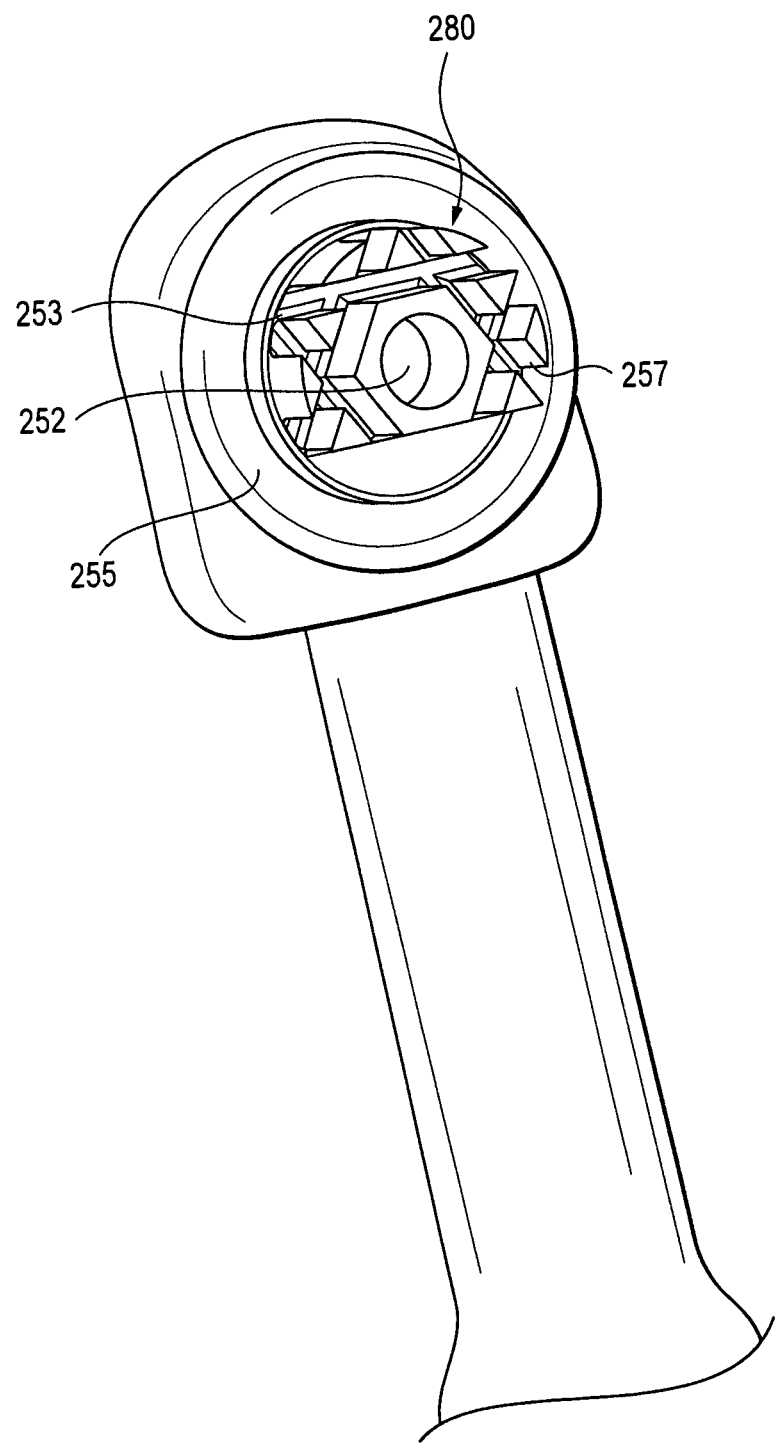
FIG. 3 illustrates a perspective view of the tip of an electrosurgical probe according to a third embodiment of the present invention.
Figure 4:
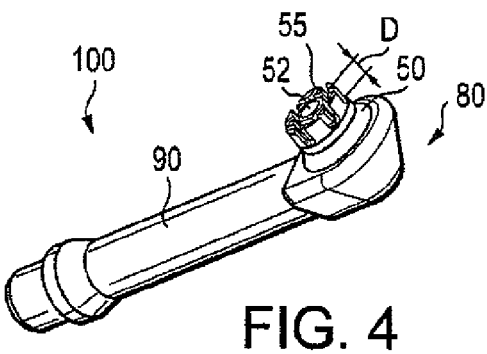
FIG. 4 illustrates a perspective view of the electrosurgical probe of FIG. 1.
Figure 5:
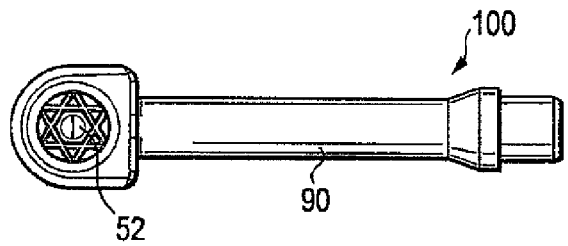
FIG. 5 illustrates a top view of the electrosurgical probe of FIG. 4.
Figure 6:
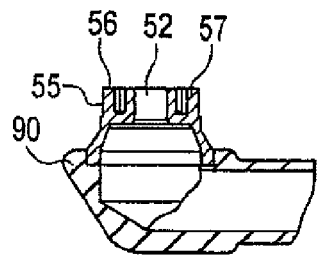
FIG. 6 illustrates a cross-sectional view of the tip of the electrosurgical probe of FIG. 5.
Figure 7:
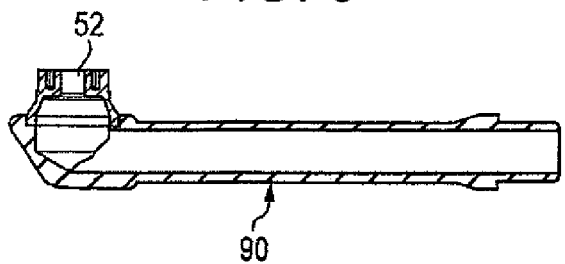
FIG. 7 illustrates a cross-sectional view of the electrosurgical probe of FIG. 5.
Figure 8:
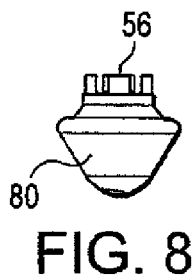
FIG. 8 illustrates a detail of the tip of the electrosurgical probe of FIG. 7.
Figure 9:
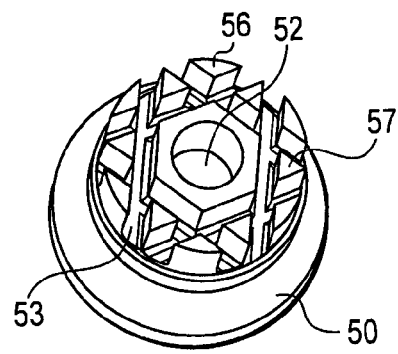
FIG. 9 illustrates a perspective view of the tip of the electrosurgical probe of FIG. 4.
Figure 10:
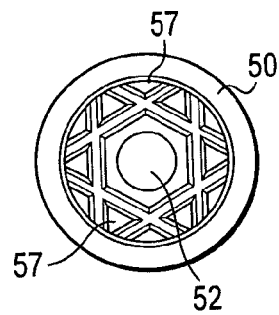
FIG. 10 illustrates a top view of the tip of FIG. 9.
Figure 11:
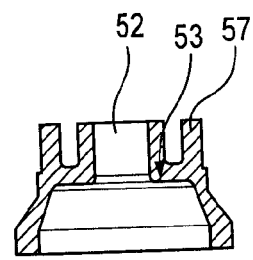
FIG. 11 illustrates a cross-sectional view of the tip of FIG. 9.
Figure 12:
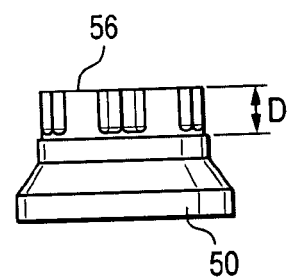
FIG. 12 illustrates a side view of the tip of FIG. 9.
Figure 13:
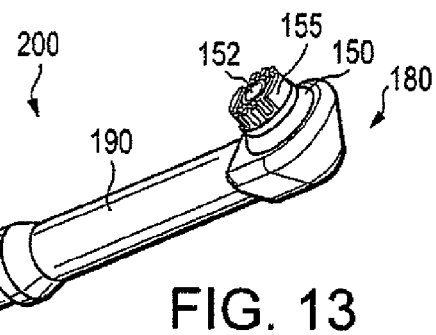
FIG. 13 illustrates a perspective view of the electrosurgical probe of FIG. 2.
Figure 14:
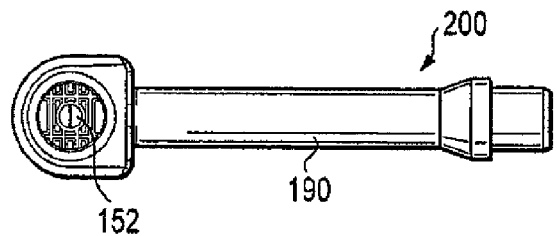
FIG. 14 illustrates a top view of the electrosurgical probe of FIG. 13.
Figure 15:
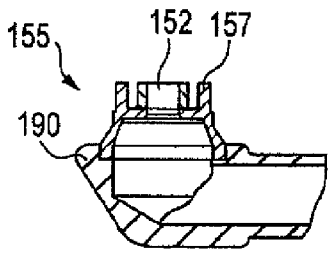
FIG. 15 illustrates a cross-sectional view of the tip of the electrosurgical probe of FIG. 14.
Figure 16:
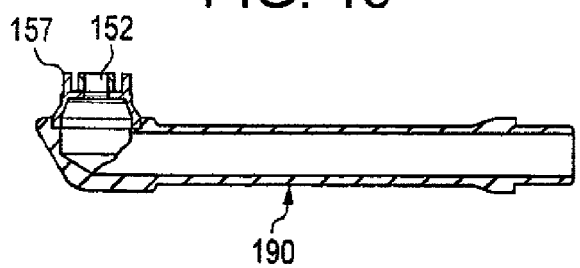
FIG. 16 illustrates a cross-sectional view of the electrosurgical probe of FIG. 14.
Figure 17:
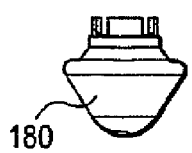
FIG. 17 illustrates a detail of the tip of the electrosurgical probe of FIG. 14.
Figure 18:
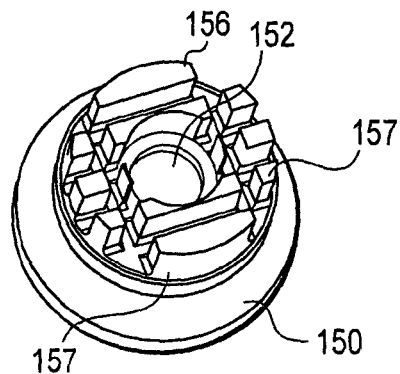
FIG. 18 illustrates a perspective view of the tip of the electrosurgical probe of FIG. 13.
Figure 19:
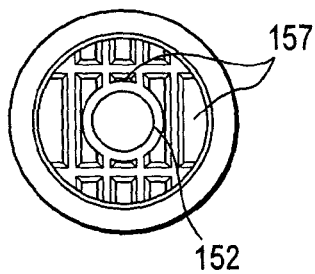
FIG. 19 illustrates a top view of the tip of FIG. 18.
Figure 20:
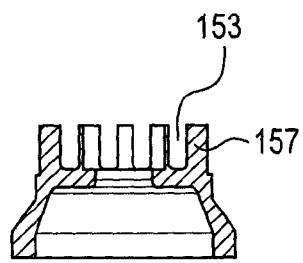
FIG. 20 illustrates a cross-sectional view of the tip of FIG. 18.
Figure 21:
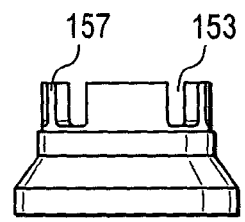
FIG. 21 illustrates a side view of the tip of FIG. 18.

FIGS. 1-3 illustrate three exemplary embodiments of monopolar electrosurgical probes 100, 200 and 300, respectively, that may be employed as part of the electrosurgical system 101 (FIG. 22) for the treatment of body tissue in minimally invasive procedures within the body. For example, electrosurgical probes 100, 200, 300 of the present invention may be employed in procedures that require the introduction of a surgical instrument through a percutaneous penetration or through a natural opening in the patient.

The monopolar electrosurgical probe 100 of FIG. 1 is illustrated in more detail in FIGS. 4-12. Probe 100 comprises an elongated distal shaft 90 having a proximal end adjacent an electrical connector, for example, and a distal end in contact with or near a distal active electrode 80. The elongated distal shaft 90 may have a variety of configurations for mechanically supporting the distal active electrode 80 and permitting a treating physician to manipulate the distal active electrode 80 from a proximal end of the shaft. Preferably, the elongated distal shaft 90 may be a tube or a narrow-diameter rod, which may be bent or curved, for example, and which may have dimensions that permit the distal active electrode 80 to be introduced through an associated cannula in a minimally invasive procedure (such as arthroscopic or other endoscopic procedures) or into a body cavity (such as the abdominal cavity).

The elongated distal shaft 90 may be flexible or rigid, or may be formed as a combination of a flexible shaft combined with a generally rigid external tube for increased mechanical and physical support. The elongated distal shaft 90 may also include pull wires or shape memory actuators or other known mechanisms for facilitating the positioning of the distal active electrode 80 in the vicinity of the target tissue.

Although, for simplicity, the embodiments of the present invention will be described below with reference to only one distal active electrode 80 as part of the electrosurgical probe 100, the invention is not limited to this exemplary embodiment. Accordingly, the invention also contemplates the formation of a plurality of such distal active electrodes 80 as part of an electrosurgical electrode.

According to an exemplary embodiment of the present invention, the distal active electrode 80 of the electrosurgical probe 100 comprises a dielectric material 50, a metallic tip 55 extending from within the dielectric material 50, and a central lumen 52 for directing aspiration flow (preferably, a central lumen or "chimney") provided through the metallic tip.

The dielectric material 50 may comprise an electrically insulating material such as epoxy, plastic, silicon-based material, ceramic, glass or compositions of these mentioned materials, among many others. The dielectric material 50 surrounds and insulates the metallic tip 55 of the probe.

The central lumen 52 for directing aspiration flow may have various cross-sectional shapes and geometries, for example, cylindrical or ellipsoidal, among others. For electrosurgical probes with larger electrode face configurations, a suction bore range of about 0.041 inches to about 0.031 inches is preferred, the optimal suction bore being about 0.037 inches. For electrosurgical probes with smaller electrode face configurations, a suction bore of about 0.31 inches is preferred. The preferred wall thickness surrounding the suction port is in the range of about 0.002 inches to about 0.010 inches, with an optimal thickness of about 0.005 inches.

The central lumen 52 may be made from a suitable electrically conductive material including, but not limited to, metallic material such as, for example, stainless steel, nickel, titanium or tungsten, or alternatively from a ceramic materials such as alumina or zirconia. In yet other embodiments, the central lumen 52 may comprise a combination of at least a metallic material and at least a ceramic material.

The central lumen or "chimney" referenced in this application may have various shapes and different cross-sections when viewed in plan view. For example, lumen 52 may be round, but the outer shape may have a rectangular cross-section, a square, a hexagonal, or an ellipsoidal shape, among many others. Preferably, the outer shape, i.e., the outer surface of lumen 52, is hexagonal to accommodate the "star-shaped" or partial "star-shaped" design of the tip of the electrode. The wall thickness of the aspiration member may be constant (as for lumen 52), or may vary depending on the lumen and outer shape cross-sections. As noted above, the thickness of aspiration lumen 52 is preferably between about 0.08 mm to about 1.5 mm, and more preferably between about 0.1 mm to about 0.6 mm. In exemplary embodiments, the aspiration member may be provided as a separate component, or constructed integral with the active electrode (as a one-piece assembly, for example).

As described in more detail below, the central lumen 52 advantageously allows surgical fluids and debris to be aspirated from an ablation site with a "self-cleaning" effect. The central lumen for directing aspiration flow is circumferentially surrounded by a plurality of protuberances having various geometries and being spaced from each other by a plurality of grooves. Preferably, and as described below, the plurality of protuberances are provided in a "star-shaped" or partial "star-shaped" pattern having at least two substantially parallel recesses and at least two substantially non-parallel recesses, to provide consistent and aggressive suction, and to maintain a cool environment, while simultaneously delivering a controlled therapeutic effect at low power.

Protuberances 57 are provided at the metallic tip 55 located at the distal end of the dielectric material 50 and are spaced from each other and surrounded by a plurality of open grooves 53. The protuberances 57 surround the central lumen for directing aspiration flow 52. Although protuberances 57 of FIGS. 4-12 are illustrated as having the shapes and geometries forming the specific "star-shaped" design of FIG. 9, the protuberances and the corresponding grooves around them may be designed to have any other shape, such as the partial "star-shaped" design of FIG. 3, or a trapezoidal, triangular, square, hexagonal, round, or ellipsoidal shape, for example, to form a specific design that would allow decreased electrode area and increased ablation efficiency.

Protuberances 57 are preferably formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, or combinations of such metals and metal alloys, among others.

Although contact surface 56 of the metallic protuberances 57 is illustrated in FIGS. 4-12 as a planar surface, the geometry of this contact surface may vary, primarily according to the location of the target tissue to be treated. Thus, contact surface 56 may be also concave, convex, hemispherical or conical, among many others.

As illustrated in FIGS. 4-7, the distal transverse surface of the metallic protuberances 57 (i.e., the contact surface 56) is about coplanar with the distal transversal surface of the central lumen 52. The protuberances 57 and the central lumen 52 protrude above the distal surface of the dielectric material 50 by a distance "D" (FIG. 4) of less than about 0.5 mm to about 1 mm, preferably of about 0.5 mm.

FIGS. 13-21 illustrate another exemplary embodiment of electrosurgical probe 200 according to the present invention. Distal active electrode 180 of the electrosurgical probe 200 comprises protuberances 157 spaced apart from each other and surrounded by a plurality of grooves 153, as shown in the design illustrated in FIGS. 13-21. Central lumen 152 is provided through metallic tip 155.

A third exemplary embodiment of electrosurgical probe 300 according to the present invention is illustrated in FIG. 3. The partial "star-shaped" design of the distal active electrode 280 of the electrosurgical probe 300 includes metallic protuberances 257 spaced apart from each other and surrounded by a plurality of grooves 253. Central lumen 252 is provided through metallic tip 255. The partial "star-shaped" design of the distal active electrode 280 has a decreased metallic electrode area compared to the designs of the electrodes of FIGS. 1 and 2. The decreased electrode area leads to a substantial increase in the probe impedance and, in turn, to increased efficiency and high ablation rates.

As a result of the improved design of the metallic tip illustrated above, the electrosurgical probe 100, 200, 300 of the present invention operates effectively at low RF power when the electrosurgical probe is brought in contact with a tissue. In addition, the shape of the metallic protuberances generate grooves in the metallic electrode which increase the probe area for trapping heated liquid and generating bubble and spark formation when the electrosurgical probe 100, 200, 300 is brought in contact with a tissue to be treated. Thus, as a result of the increased ability to trap bubbles and generate sparks at the tip of the metallic electrode, less power is needed to create bubbles than in a conventional probe.

Increasing the impedance of the electrosurgical probe 100 and the ability to trap steam bubbles further reduces the ignition problems associated with conventional electrosurgical probes, therefore making the operation of the electrosurgical probe 100, 200, 300 more controlled. Since the necessary RF power is smaller than that of a conventional probe, a surgeon conducting a procedure employing the electrosurgical probe 100, 200, 300 of the present invention has a larger margin of safety, which in turn reduces the chances of patient burns. The contact time between the electrosurgical probe of the present invention and the tissue to be treated is also decreased.

The unique electrode configuration of the present invention advantageously provides a "sweeping effect" of steam bubbles created along the slot edges across the electrode face for enhanced "firing" capabilities, while creating a "chimney effect" in close proximity to the hot active electrode face that results in a "self-clearing" capability and avoids clogging of the suction port. By positioning the suction port in the center of, and surrounded by, the active electrode, any potential aspiration clog is cleared by a combination of the continued transference of heat created as a byproduct of the RF therapeutic effect, which causes tissue in the suction port to become denatured and then forcefully drawn through the device by the vacuum. Accordingly, the electrosurgical probe of the present invention is better able to provide an aggressive suction effect within the joint space to maintain a cool environment, which also providing a controlled therapeutic ablation effect at low power without the inconvenience of having to address device clogs.

The high efficiency electrosurgical probe 100, 200, 300 of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

Surgical procedures using the electrosurgical probe 100, 200, 300 of the invention include introducing the probe assembly in close proximity to the surgical site through an artificial conduit or a cannula, or through a natural conduit which may be in an anatomical body cavity or space or one created surgically. For the purposes of the present invention, the terms "close proximity" and "proximity" are defined as "in contact with" or "at a distance of about 0.1 to about 20 millimeters." The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 23:
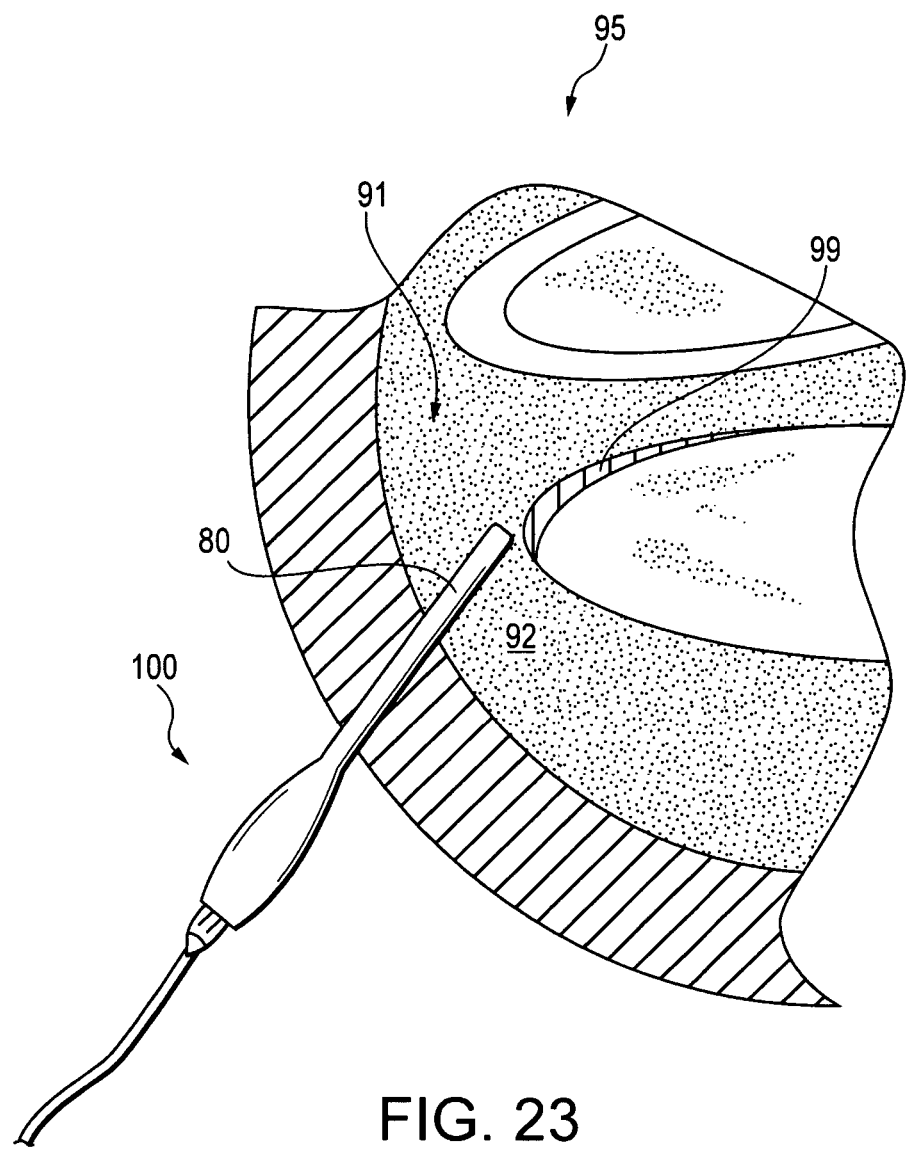
FIG. 23 is a schematic cross-sectional view of a knee joint undergoing an electrosurgical procedure employing an electrosurgical electrode of the present invention.

To better illustrate an exemplary surgical procedure conducted with the "self-cleaning" electrosurgical ablator 100 of the present invention, reference is now made to FIG. 23, which illustrates a schematic cross-sectional view of a knee joint region 95. The knee joint region 95 of FIG. 23 may undergo an arthroscopic procedure, for example, with electrosurgical ablator 100 fabricated according to the present invention. As known in the art, an endoscope (not shown) may be provided at one end with the distal active electrode piece 80 having aspiration lumen 52 and protuberances 57 preferably provided in a "star-shaped" design, and then introduced into knee cavity 92 (FIG. 23) containing electrically conductive fluid 91 (FIG. 23) and in close proximity to target tissue 99 (FIG. 23). If the target tissue 99 of the knee joint region 95 is a damaged meniscus, for example, then target tissue 99 may undergo a partial or complete electrosurgical meniscectomy using active electrode 80. Alternatively, the endoscope may be introduced separately from the electrosurgical electrode, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once distal active electrode 80 is positioned in the proximity of the target tissue 99 and the target tissue 99 is submerged in the electrically conductive fluid 91, the electrosurgical probe is energized by the electrosurgery power supply. The power supply delivers radio frequency energy, typically in the range of 100 kHz to 3 MHz, through a cable system to the electrosurgical electrode 100 and further to the distal active electrode 80.

Although the present invention has been described in relation to particular embodiments thereof, many other variations and modifications and other uses will become apparent to those skilled in the art. Any modification of the present invention which comes within the spirit and scope of the following claims should be considered part of the present invention.

What is claimed is:

1. An electrosurgical ablator comprising:
a shaft having a proximal end and a distal end; and
at least one active electrode located at or near said distal end of the shaft including an electrically conductive tip, the at least one active electrode comprising a plurality of protuberances spaced from each other and defining a plurality of recesses therebetween, wherein the plurality of protuberances protrude from a surface of the at least one active electrode,
wherein the electrically conductive tip further comprises a centrally located aspiration port separated from adjacent recesses of the plurality of recesses, wherein the plurality of protuberances define a tissue contact surface that is flat and planar, and the centrally located aspiration port is separated from the adjacent recesses by a wall that surrounds the centrally located aspiration port, and
wherein the plurality of protuberances and recesses are provided in a star-shaped pattern or a partial star-shaped pattern, at least two of the plurality of recesses are substantially non-parallel, and at least two of the plurality of recesses are substantially parallel, and at least some of the plurality of recesses define a path that at least partially surrounds the centrally located aspiration port.

2. The electrosurgical ablator of claim 1, wherein the centrally located aspiration port comprises a central tubular member.

3. The electrosurgical ablator of claim 2, wherein the wall has an outer surface and an inner surface, wherein the outer surface has a regular polygonal shape or a circular shape when viewed in a cross-sectional view.

4. The electrosurgical ablator of claim 3, wherein the regular polygonal shape is a hexagonal shape.

5. The electrosurgical ablator of claim 2, wherein the central tubular member comprises a material which is similar to that of the plurality of protuberances.

6. The electrosurgical ablator of claim 2, wherein the central tubular member comprises a material which is different from that of the plurality of protuberances.

7. The electrosurgical ablator of claim 2, wherein the central tubular member has a cross-sectional shape selected from the group consisting of rectangular, square, circular, trapezoidal, triangular, hexagonal and ellipsoidal shape, and a combination of such shapes.

8. The electrosurgical ablator of claim 2, wherein the central tubular member has a cross-sectional shape that is a regular polygonal shape.

9. The electrosurgical ablator of claim 2, wherein the central tubular member has a cross-sectional shape that is an irregular polygonal shape.

10. The electrosurgical ablator of claim 1, wherein the centrally located aspiration port is integral with the active the at least one active electrode.

11. The electrosurgical ablator as recited in claim 1, wherein the plurality of protuberances protrude upwardly from the surface of the at least one active electrode.

12. The electrosurgical ablator of claim 1, wherein at least one of the plurality of protuberances is triangular.

13. The electrosurgical ablator as recited in claim 1, wherein the plurality of protuberances comprise a hexagonal protuberance that surrounds the centrally located aspiration port and six triangular shaped protuberances that surround the hexagonal protuberance, and a continuous path is defined between the six triangular shaped protuberances and the hexagonal protuberance.

14. The electrosurgical ablator of claim 1, wherein an outer side surface of the plurality of protuberances is perpendicular to the tissue contact surface.

15. The electrosurgical ablator of claim 1, wherein each of the plurality of recesses include an exposed opening located between two of the plurality of protuberances.

16. The electrosurgical ablator as recited in claim 1, wherein at least one of the plurality of protuberances includes an outer side surface that is exposed.

17. The electrosurgical ablator of claim 1, wherein the plurality of protuberances are surrounded by and extend from a dielectric material.

18. The electrosurgical ablator as recited in claim 17, wherein the dielectric material contacts the at least one active electrode.

19. The electrosurgical ablator as recited in claim 1, wherein at least some of the plurality of recesses define a path that completely surrounds the centrally located aspiration port.

20. The electrosurgical ablator as recited in claim 1, wherein the electrosurgical ablator is mono-polar.

21. The electrosurgical ablator as recited in claim 1, wherein the electrosurgical ablator is configured to ablate tissue at the tissue contact surface.

22. The electrosurgical ablator as recited in claim 1, wherein each of the plurality of recesses are straight and defined by at least two parallel surfaces, and the at least two parallel surfaces are each a part of one of the plurality of protuberances.

23. An electrosurgical ablator comprising:
a shaft having a proximal end and a distal end; and
at least one active electrode located at or near said distal end of the shaft including an electrically conductive tip, the at least one active electrode comprising a plurality of protuberances spaced from each other and defining a plurality of recesses therebetween, wherein the plurality of protuberances protrude from a surface of the at least one active electrode, at least two of the plurality of recesses are substantially non-parallel, and at least two of the plurality of recesses are substantially parallel, wherein the electrically conductive tip further comprises a centrally located aspiration port separated from adjacent recesses of the plurality of recesses, wherein the centrally located aspiration port comprises a central tubular member having a distal surface, and the plurality of protuberances have a transverse distal surface, the distal surface of the central tubular member being about equal in height with the transverse distal surface of the plurality of protuberances,
wherein the plurality of protuberances and recesses are provided in a star-shaped pattern or a partial star-shaped pattern.

24. The electrosurgical ablator as recited in claim 23, wherein each of the plurality of recesses are straight and defined by at least two parallel surfaces, and the at least two parallel surfaces are each a part of one of the plurality of protuberances.

* * * * *